US008921633B2

(12) United States Patent
Iaccino et al.

(10) Patent No.: US 8,921,633 B2
(45) Date of Patent: Dec. 30, 2014

(54) PROCESS FOR THE PRODUCTION OF XYLENES AND LIGHT OLEFINS

(75) Inventors: Larry L. Iaccino, Seabrook, TX (US);
Stephen M. Davis, Humble, TX (US);
Steven E. Silverberg, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 360 days.

(21) Appl. No.: 13/465,750

(22) Filed: May 7, 2012

(65) Prior Publication Data
US 2013/0296623 A1 Nov. 7, 2013

(51) Int. Cl.
| C10G 9/00 | (2006.01) |
| C10B 55/00 | (2006.01) |
| C10G 69/04 | (2006.01) |
| C10G 69/06 | (2006.01) |
| C10G 69/08 | (2006.01) |
| C10G 47/00 | (2006.01) |
| C10G 49/22 | (2006.01) |
| C10G 11/14 | (2006.01) |
| C10G 11/05 | (2006.01) |
| C07C 7/12 | (2006.01) |
| C07C 21/00 | (2006.01) |
| C07C 2/64 | (2006.01) |
| C07C 2/86 | (2006.01) |

(52) U.S. Cl.
CPC .. *C07C 2/64* (2013.01); *C07C 2/864* (2013.01)
USPC ............ 585/321; 585/322; 585/323; 208/50; 208/60; 208/61; 208/62; 208/67; 208/100; 208/102; 208/113; 208/160; 208/310 R; 208/312

(58) Field of Classification Search
USPC ........... 208/50, 60, 61, 62, 67, 100, 102, 113, 208/160, 310 R, 312; 585/322, 323
See application file for complete search history.

(56) References Cited

U.S. PATENT DOCUMENTS

| 2,415,272 | A | | 2/1947 | Benedict et al. |
| 3,409,540 | A | * | 11/1968 | Gould et al. ............. 208/60 |
| 3,862,898 | A | | 1/1975 | Boyd et al. |
| 3,894,934 | A | | 7/1975 | Owen et al. |
| 4,053,388 | A | | 10/1977 | Bailey |
| 4,058,450 | A | | 11/1977 | Le Page et al. |
| 4,058,454 | A | | 11/1977 | Asselin |
| 4,078,990 | A | | 3/1978 | Brennan et al. |
| 4,257,871 | A | | 3/1981 | Wernicke et al. |
| 4,980,053 | A | | 12/1990 | Li et al. |
| 5,043,502 | A | | 8/1991 | Martindale et al. |
| 5,232,675 | A | | 8/1993 | Shu et al. |
| 5,326,465 | A | | 7/1994 | Yongqing et al. |
| 5,358,918 | A | | 10/1994 | Yukang et al. |
| 5,380,690 | A | | 1/1995 | Zhicheng et al. |
| 5,932,777 | A | | 8/1999 | Sughrue et al. |
| 6,077,984 | A | | 6/2000 | Drake et al. |
| 6,080,698 | A | | 6/2000 | Zhang et al. |
| 6,114,592 | A | | 9/2000 | Gajda et al. |
| 6,153,089 | A | | 11/2000 | Das et al. |
| 6,210,562 | B1 | | 4/2001 | Xie et al. |
| 6,211,104 | B1 | | 4/2001 | Shi et al. |
| 6,342,153 | B1 | | 1/2002 | Guan et al. |
| 6,420,621 | B2 | | 7/2002 | Sha et al. |
| 6,504,073 | B1 | | 1/2003 | Ushio et al. |
| 6,635,792 | B2 | | 10/2003 | Choi et al. |
| 6,740,788 | B1 | | 5/2004 | Maher et al. |
| 7,119,239 | B2 | | 10/2006 | Johnson et al. |
| 7,153,478 | B2 | | 12/2006 | Xu et al. |
| 7,176,339 | B2 | | 2/2007 | Iaccino et al. |
| 7,179,434 | B1 | | 2/2007 | Maher et al. |
| 7,288,687 | B1 | | 10/2007 | Frey et al. |
| 7,297,831 | B2 | | 11/2007 | Lee et al. |
| 7,301,063 | B2 | | 11/2007 | Choi et al. |
| 7,396,967 | B2 | | 7/2008 | Iaccino et al. |
| 7,553,791 | B2 | | 6/2009 | McMinn et al. |
| 7,563,358 | B2 | | 7/2009 | Stavens et al. |
| 7,578,929 | B2 | | 8/2009 | Stell et al. |
| 7,601,311 | B2 | | 10/2009 | Casey et al. |
| 7,629,498 | B2 | | 12/2009 | Brown et al. |
| 7,727,490 | B2 | | 6/2010 | Zhou |
| 7,923,399 | B2 | | 4/2011 | Long et al. |
| 7,972,498 | B2 | | 7/2011 | Buchanan et al. |
| 8,183,424 | B2 | | 5/2012 | Levin et al. |
| 2001/0053868 | A1 | | 12/2001 | Chester et al. |
| 2003/0105372 | A1 | | 6/2003 | Feng et al. |
| 2003/0116471 | A1 | | 6/2003 | Zhang et al. |
| 2004/0049093 | A1 | | 3/2004 | Cheung et al. |
| 2005/0020867 | A1 | | 1/2005 | Xie et al. |
| 2005/0209495 | A1 | | 9/2005 | McCoy et al. |

(Continued)

FOREIGN PATENT DOCUMENTS

| AU | 776 247 | 9/2004 |
| EP | 0136072 | 4/1985 |

(Continued)

OTHER PUBLICATIONS

U.S. Appl. No. 61/421,917, filed Dec. 10, 2010, Ellrich et al.

*Primary Examiner* — Randy Boyer (57) ABSTRACT

In a hydrocarbon upgrading process, a hydrocarbon feed is treated in at least one of a steam cracker, catalytic cracker, coker, hydrocracker, and reformer under suitable conditions to produce a first stream comprising olefinic and aromatic hydrocarbons. A second stream composed mainly of $C_4$ to $C_{12}+$ olefinic and aromatic hydrocarbons is recovered from the first stream and blended said second stream with a residual fraction from a steam cracker or an atmospheric or vacuum distillation unit to produce a third stream. The third stream is then catalytically pyrolyzed in a reactor under conditions effective to produce a fourth stream having an increased benzene and/or toluene content compared with said second stream and a $C_3$-olefin by-product. The $C_3$-olefin by-product is recovered and benzene and/or toluene are recovered from the fourth stream.

18 Claims, 1 Drawing Sheet

(56) References Cited

U.S. PATENT DOCUMENTS

| | | |
|---|---|---|
| 2006/0194996 A1 | 8/2006 | Umansky et al. |
| 2008/0249345 A1 | 10/2008 | Kin et al. |
| 2009/0000988 A1 | 1/2009 | Brown et al. |
| 2010/0040517 A1 | 2/2010 | Brown et al. |
| 2012/0149958 A1 | 6/2012 | Ellrich et al. |

FOREIGN PATENT DOCUMENTS

| | | |
|---|---|---|
| EP | 1068166 | 3/2004 |
| KR | 10-0632571 | 10/2006 |
| WO | 01/79383 | 10/2001 |
| WO | WO 2007/108573 | 9/2007 |
| WO | WO 2012/015541 | 2/2012 |

\* cited by examiner

PROCESS FOR THE PRODUCTION OF XYLENES AND LIGHT OLEFINS

STATEMENT OF RELATED CASES

This application is related to U.S. Ser. No. 13/303,855, filed Nov. 23, 2011 which claims the benefit of and priority to U.S. Ser. No. 61/421,917 filed Dec. 10, 2010.

FIELD OF THE INVENTION

The invention relates to a process for the production of xylenes and light ($C_4-$) olefins from diverse olefinic refinery feedstocks.

BACKGROUND OF THE INVENTION

Xylene isomers find wide and varied application. They are especially valuable as intermediates in chemical processes. By way of example, para-xylene (PX) is a feedstock for terephthalic acid, which finds use in the manufacture of polyester fibers and films; meta-xylene (MX) is used in the manufacture of dyes; and ortho-xylene (OX) is used as a feedstock for phthalic anhydride, which finds use in the manufacture of plasticizers. PX is currently the most valuable of the xylene isomers and, although research related to obtaining (e.g., producing or purifying) PX is too voluminous to mention, there is still intensive research in the area.

There are many possible feeds currently used to obtain PX. The majority of para-xylene produced today comes from catalytic reforming, which involves dehydrogenation and dehydrocyclization of naphtha feedstocks. The effluent of the reforming process, known as reformate, is rich in aromatics, particularly benzene, toluene, and mixed xylenes (BTX), and is used as feedstock to aromatics plants. Processes exist to increase the yield of para-xylene over the equilibrium mixture in the reformate, including selective toluene, disproportionation and selective methylation of benzene and/or toluene with methanol.

Recently, significant research has focused on finding alternative sources and methods for producing BTX and particularly para-xylene. For example, although steam cracking, or pyrolysis, is the preferred method of producing light olefins (ethylene, propylene, and butenes) from heavier hydrocarbon feedstocks, the process also generates a by-product termed pyrolysis gasoline, steam cracked naphtha (SCN) or pygas. Pygas is a complex mixture of $C_6$ to $C_{10}+$ hydrocarbons that is rich in aromatics, particularly benzene and toluene, but also contains $C_8$, $C_9$, and $C_{10}+$ aromatics. Similarly, catalytic cracking, particularly fluid catalytic cracking (FCC), in addition to producing fuels and light olefins, generates a $C_6$ to $C_{10}$ aromatic rich stream which is similar to pygas and is generally known as cat naphtha. There is significant interest in developing methods of upgrading refinery sources, such as pygas and cat naphtha, to increase the yield of BTX and preferably para-xylene.

For example, U.S. Pat. No. 6,635,792 discloses a process for producing BTX and liquefied petroleum gas (LPG) from a hydrocarbon feedstock having boiling points of 30° C. to 250° C., such as reformate and pyrolysis gasoline. In the process, aromatic components in the hydrocarbon feedstock are converted to BTX-enriched components in the liquid phase through hydrodealkylation and/or transalkylation, and non-aromatic components are converted to LPG-enriched gaseous materials through hydrocracking. The process employs a catalyst comprising platinum/tin or platinum/lead on mordenite, zeolite beta or ZSM-5. U.S. Pat. Nos. 7,297,831 and 7,301,063 disclose similar processes.

U.S. Pat. No. 7,563,358 discloses a process for producing BTX-enriched product from a hydrocarbon feed comprising: (a) $C_6+$ non-aromatic cyclic hydrocarbons; (b) $C_8+$ single-ring aromatic hydrocarbons having at least one alkyl group containing two or more carbon atoms; and (c) $C_9+$ single-ring aromatic hydrocarbons having at least three methyl groups, by contacting the feed in the presence of hydrogen with a catalyst comprising at least one Group VIII metal and a large or intermediate pore molecular sieve having an alpha value, before incorporation of the Group VIII metal, from about 2 to less than 100 under conditions sufficient for (i) forming aromatic hydrocarbons from $C_6+$ non-aromatic cyclic hydrocarbons; (ii) dealkylating $C_8+$ single-ring aromatic hydrocarbons having at least one alkyl group containing two or more carbon atoms; (iii) transalkylating $C_9+$ single-ring aromatic hydrocarbons having at least three methyl groups; and (iv) disproportionating toluene, to produce a product containing an increased amount of BTX compared to the feed. A preferred hydrocarbon feed is steam cracked naphtha.

Although steam cracked naphtha is an excellent source of BTX in the refinery, it will be understood the feedstock for a conventional steam cracking unit must be subjected to substantial (and expensive) processing before it reaches the unit. Normally, whole crude is first subjected to desalting prior to being distilled or otherwise fractionated or cracked into a plurality of fractions, such as gasoline, kerosene, naphtha, gas oil (vacuum or atmospheric), and the like, including a high boiling residuum ("resid"). The resid cut typically has a boiling point of greater than about 650° F. (343° C.), at about atmospheric pressure. After desalting and removal of the resid fractions, any of the remaining fractions other than the 650° F.+(343° C.+) resid, may be passed to a steam cracker as the feedstock for that plant. Such resid fractions are, however, also potential sources of BTX and/or olefins although, in view of their highly viscous nature, they normally require expensive pretreatment by hydrotreating and/or visbreaking before they can be processed.

For example, U.S. Pat. No. 7,972,498 discloses a process for producing olefins comprising: (i) hydroprocessing a feed comprising crude comprising resid or a crude fraction comprising resid in a hydroprocessing unit at a temperature sufficient to promote incipient thermal cracking of the resid, wherein the resid includes 1050° F.+(565° C.+) resid; (ii) obtaining hydrogenated $C_2+$ effluent from a resid hydroprocessing unit, wherein the effluent comprises resid; (iii) separating the effluent in a separator that comprises at least one of a visbreaker, a flash drum, a high pressure separator, and a vapor liquid separator wherein the effluent in the separator is heated at visbreaking conditions to a temperature of at least about 850° F. (454° C.), into an overhead stream and a bottoms stream, the bottoms stream comprising hydroprocessed resid including 1050° F.+(565° C.+) resid; (iv) feeding the overhead stream as vapor to a steam cracker; (v) steam cracking the overhead stream and obtaining a steam cracker effluent from the steam cracker comprising olefins; (vi) feeding the bottoms stream to a catalytic cracking unit; and (vii) cracking the bottoms stream in the catalytic cracking unit to obtain a catalytically cracked stream comprising at least one of gas oil and olefins; and further comprising flashing the effluent through at least one pressure drop to reduce the pressure of the effluent, prior to or during the step of separating the effluent. U.S. Pat. No. 4,257,871 discloses a process for producing olefins from a vacuum residue by first separating, preferably by solvent extraction, the asphalt therein, blending resultant asphalt-depleted fraction with a lighter fraction, e.g., a vacuum gas oil, and then subjecting the blend to a conventional catalytic hydrogenation step prior to thermal cracking.

In addition, U.S. Published Patent Application No. 2005/0209495 discloses process for steam cracking a heavy hydrocarbon feedstock, said process comprising: (a) heating a heavy hydrocarbon feedstock; (b) mixing the heavy hydrocarbon feedstock with a fluid to form a mixture stream; (c) flashing the mixture stream to form a vapor phase and a liquid phase; (d) removing the liquid phase in a flash/separation vessel; (e) cracking the vapor phase in a radiant section of a pyrolysis furnace to produce an effluent comprising olefins, said pyrolysis furnace comprising a radiant section and a convection section; and (f) quenching the effluent using a transfer line exchanger, wherein the amount of the fluid mixed with the heavy hydrocarbon feedstock is varied in accordance with at least one selected operating parameter of the process.

Additional references of interest include: U.S. Pat. No. 7,176,339.

According to the present invention, it has now been found that by blending resid fractions with pyrolysis gasoline and/or similar aromatic refinery streams, the viscosity of the blend can be reduced sufficiently to allow the blend to be fed to a catalytic pyrolysis unit to produce an effluent stream with an increased benzene and/or toluene content and a $C_3-$ olefin by-product.

SUMMARY OF THE INVENTION

Accordingly, the invention resides in one aspect in a hydrocarbon upgrading process comprising:

(a) treating a hydrocarbon feed in at least one of a steam cracker, catalytic cracker, coker, hydrocracker, and reformer under suitable conditions to produce a first stream comprising olefinic and aromatic hydrocarbons;

(b) recovering from said first stream a second stream composed mainly of $C_4$ to $C_{12}$ olefinic and aromatic hydrocarbons;

(c) blending said second stream with a residual fraction from a steam cracker or an atmospheric or vacuum distillation unit to produce a third stream;

(d) catalytically pyrolyzing said third stream in a reactor under conditions effective to produce a fourth stream having an increased benzene and/or toluene content compared with said second stream and a $C_3-$ olefin by-product;

(e) recovering $C_3-$ olefins from said fourth stream; and (f) recovering benzene and/or toluene from said fourth stream.

Conveniently, the hydrocarbon feed is selected from natural gas liquids, natural gas condensate, naphtha, distillate, gas oils, crude oil, and/or resid.

In one embodiment, the residual fraction comprises heavy tar produced as the product of steam cracking and/or the bottoms product of a vapor liquid separator drum integrated into the steam cracker.

Conveniently, the catalytic pyrolysis is conducted in the presence of a catalyst comprising ZSM-5 and, optionally a large pore and/or an amorphous cracking component, under reaction conditions including a temperature of about 480° C. to about 750° C. Generally, the catalytic pyrolysis is conducted in a riser reactor. In one embodiment, part of the catalyst is removed from the reactor and contacted with an oxygen-containing stream to remove coke from the catalyst and heat the catalyst thereby providing a portion of the heat required for (d).

Conveniently, the process further comprises removing $C_4$ and $C_5$ hydrocarbons and/or $C_8+$ hydrocarbons from the fourth stream and recycling said $C_4$ and $C_5$ and/or $C_8+$ hydrocarbons to (d).

Conveniently, benzene and/or toluene are recovered from said fourth stream by separating a $C_6$ and/or $C_7$ fraction from the fourth stream and removing aliphatic hydrocarbons from the $C_6$ and/or $C_7$ fraction to leave an aliphatics-depleted fraction. Generally, the aliphatic hydrocarbons are removed from the $C_6$ and $C_7$ fraction by solvent extraction or selective adsorption and are recycled to (d).

In one embodiment, the process further comprises methylating benzene and/or toluene recovered in (f) with a methylating agent, such as methanol, to produce a xylene-enriched stream and recovering para-xylene from said xylene-enriched stream.

DETAILED DESCRIPTION OF THE EMBODIMENTS

As used herein, the term "$C_n$" hydrocarbon wherein n is a positive integer, e.g., 1, 2, 3, 4, 5, 6, 7, 8, 9, 10, 11, 12, means a hydrocarbon having n number of carbon atom(s) per molecule. The term "$C_n+$" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n-$" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

Described herein is hydrocarbon upgrading process, in which a hydrocarbon feed is treated in at least one of a steam cracker, catalytic cracker, coker, hydrocracker, and reformer under suitable conditions to produce a first stream enriched in olefinic and/or aromatic hydrocarbons. A second stream composed mainly of $C_4$ to $C_{12}+$ olefinic and aromatic hydrocarbons is separated from the first stream and blended with a residual fraction from a steam cracker or an atmospheric or vacuum distillation unit to produce a third stream. The third stream is catalytically pyrolyzed in a reactor under conditions effective to produce a fourth stream having an increased benzene and/or toluene content compared with said second stream and a $C_4$-olefin by-product. The light (e.g. $C_4-$) olefin by-product is recovered for use as a chemical feedstock, whereas the benzene and/or toluene are removed from the fourth stream and are methylated to produce para-xylene.

Hydrocarbon Feedstock

Any hydrocarbon composition conventionally fed to a steam cracker, catalytic cracker, coker, hydrocracker, or reformer can be used as the hydrocarbon feed in the present process. Thus, for example, the hydrocarbon feed can comprise a natural gas liquid or condensate, naphtha, gas oil or any distillate fraction of whole crude oil, including in some cases the residual fraction remaining after an atmospheric or vacuum distillation process (i.e. resid).

Treating the hydrocarbon feed in the steam cracker, catalytic cracker, coker, hydrocracker, or reformer produces a first hydrocarbon stream having a broad spectrum of olefinic and aromatic hydrocarbons depending on the initial composition of the hydrocarbon feed and also on the unit used to process the feed. The first hydrocarbon stream is then subjected to one or more separation operations (such as by distillation column or absorber) to recover $C_3-$ olefins, such as ethylene and propylene; fuel gas; and $C_{12}+$ hydrocarbons and leave a second hydrocarbon stream composed mainly $C_4$ to $C_{12}$ aliphatic and aromatic hydrocarbons. The precise composition of the second hydrocarbon stream will depend on the initial composition of the hydrocarbon feed and on the unit used to process the feed. In fact, depending on the operating targets and efficiency of the fractionation steps used to remove these components, the second hydrocarbon stream may contain quantities (generally less than 20 wt %) of $C_3-$ and $C_{12}+$ hydrocarbons.

In one preferred embodiment, in which a steam cracker is employed as the process unit, the second hydrocarbon stream is a pyrolysis gasoline containing from about 15 wt % to about 65 wt % benzene, from about 5 wt % to about 35 wt % toluene, from about 1 wt % to about 15 wt % of $C_8+$ aromatic compounds and up to 50 wt %, typically about 1 wt % to about 15 wt %, non-aromatics depending on the composition of feedstock to the steam cracker, the intensity of the pyrolysis reaction, and the separation and processing scheme for the pygas stream.

In another preferred embodiment, in which a steam cracker is employed as the process unit, the second hydrocarbon stream is a $C_4$ to $C_{10}$ containing stream and an example composition is given in Table 1 below.

TABLE 1

| Species | Wt % |
| --- | --- |
| C4 diolefins | 10.3% |
| C4 olefins | 11.9% |
| C4 saturates | 1.1% |
| C5 cyclo-diolefins | 3.8% |
| C5 diolefins | 4.3% |
| C5 cyclo-olefins | 0.8% |
| C5 cyclo sat's | 0.0% |
| C5 olefins (other) | 2.6% |
| C5 saturates (other) | 1.0% |
| C6 cyclodiolefins | 1.6% |
| C6 cyclo-olefins | 0.3% |
| C6 cyclo-olefins | 2.0% |
| C6 olefins (other) | 0.9% |
| C6 saturates (other) | 0.8% |
| Benzene | 10.7% |
| C7 olefins | 2.4% |
| C7 saturates | 1.6% |
| Toluene | 7.6% |
| C8 olefins | 1.1% |
| C8 saturates | 0.9% |
| Ethylbenzene | 3.2% |
| Xylenes | 3.6% |
| Indanes | 7.8% |
| Isopropylbenzenes | 0.1% |
| Propylbenzenes | 0.3% |
| Trimethylbenznes | 1.8% |
| Methylethylbenzenes | 3.1% |
| Trimethylcyclohexanes | 0.0% |
| Propylcyclohexanes | 0.1% |
| Butylcyclopentane | 7.3% |
| Nonane | 0.1% |
| Methyloctanes | 0.0% |
| Dimethylheptanes | 0.0% |
| Trimethylhexanes | 0.0% |
| Naphthalene | 2.1% |
| Methylindanes | 1.8% |
| Dimethylethylbenzenes | 1.5% |
| Methylpropylbenzenes | 0.1% |
| Butylbenzenes | 0.2% |
| Decane | 0.0% |
| Methylnonanes | 0.0% |
| Dimethyloctanes | 0.0% |
| Dicyclopentanes | 1.1% |
| Total | 100.0% |

Generally, as the intensity of the pyrolysis reaction increases, which can be noted by the rising outlet temperature of the reactor or by the changing of the ratio of two products, such as propylene and methane, more aromatics will be present in the effluent. Similarly, as the weight of the feedstock to the pyrolysis furnace increases, the yield of aromatics in the pygas will also increase. Naphthas and gas oils are conventional feedstocks to steam crackers, including virgin, and hydrotreated streams. Resid-containing feeds (typically containing a lesser portion of 1050° F.+(566° C.+) resid, preferably 20 wt % or less 1050° F.+(566° C.+) resid, based upon the weight of the feed, preferably 10 wt % or less) can be processed by first passing through the convection section of the steam cracking furnace, then passing to a vapor/liquid separating drum, which can optionally be integrated with the pyrolysis furnace, to drop out the heaviest fraction.

Blending with Resid Fraction

The second hydrocarbon stream is blended with a residual fraction from either a steam cracker or an atmospheric or vacuum distillation unit to produce a third hydrocarbon stream. As used herein, the term "resid" or "residual fraction" refers to the complex mixture of heavy petroleum compounds otherwise known in the art as residuum or residual. Atmospheric resid is the bottoms product produced in atmospheric distillation when the endpoint of the heaviest distilled product is nominally 343° C., and is referred to as 343° C.+ resid. Vacuum resid is the bottoms product from a column under vacuum when the heaviest distilled product is nominally 566° C., and is referred to as 566° C.+(e.g., temperatures above 566° C.) resid. The term "nominally" means here that reasonable experts may disagree on the exact cut point for these terms, but probably by no more than ±30° C. or at most ±75° C. This 566° C.+ portion contains asphaltenes, which are problematic to the steam cracker, resulting in coking of the surfaces within the furnace. The term "resid" as used herein means the 650° F.+ (343° C.) resid and 1050° F.+ (566° C.) resid unless otherwise specified (note that 650° F.+ (343° C.+) resid comprises 1050° F.+ resid (566° C.+)).

Where the residual fraction is derived from steam cracking, it is conveniently taken from the heavy tar produced as the direct product of the steam cracking and/or from the bottoms product of the vapor liquid separator drum integrated into the steam cracker. Preferably, the residual fraction is derived from a highly paraffinic crude, such as Lacustrine or shale oil crudes. In addition, the residual fraction preferably has low metals content (<1,000 wt ppm) and low basic nitrogen content (<1,000 wt ppm). In some cases therefore it may be desirable to hydrotreat the residual fraction, prior to or after blending with the second hydrocarbon stream, to decrease its metal and basic nitrogen content and increase its hydrogen content.

The relative amounts of the second hydrocarbon stream and the residual fraction in the third hydrocarbon stream are not particularly limited but, in general, the blend should contain from about 50% to about 90% by weight of the residual fraction.

By blending the residual fraction with second hydrocarbon stream it is found that the viscosity of the third hydrocarbon stream can be reduced sufficiently to facilitate feeding the blend to the downstream process units, in this case the catalytic pyrolysis unit described in detail below. Further reduction in the viscosity of the blend can be achieved by heating the residual fraction, the second hydrocarbon stream and/or the blend to a temperature between about 300° C. and about 425° C.

Catalytic Pyrolysis

The blend of the residual fraction and the second hydrocarbon stream is fed to a catalytic pyrolysis reactor where the blend is contacted with a zeolite catalyst in the absence of added hydrogen under reaction conditions including a temperature of about 450° C. to about 760° C., such as about 550° C. to about 680° C., and a pressure of about 70 kPa to 700 kPa, such as 200 kPa to 350 kPa. Steam may also be fed to the reactor, for example, to lower the partial pressure of the hydrocarbon feed.

The catalyst is normally contained in a moving bed, such as a riser, a dilute fluid bed, a dense bed, or a combination thereof, and typically comprises a medium-pore size aluminosilicate zeolite, optionally in combination with a large-pore size aluminosilicate zeolite or an amorphous cracking catalyst.

Medium pore zeolites are generally defined as those having a pore size of about 5 to 7 Angstroms, such that the zeolite freely sorbs molecules such as n-hexane, 3-methylpentane, benzene, and p-xylene. Another common definition for medium pore zeolites involves the Constraint Index test, which is described in U.S. Pat. No. 4,016,218, which is incorporated herein by reference, as measured on the zeolite alone without any treatment to adjust the diffusivity of the catalyst. In this case, medium pore zeolites have a Constraint Index of 3 to about 12, as measured on the zeolite alone without any treatment to adjust the diffusivity of the catalyst. Particular examples of suitable medium pore zeolites include ZSM-5, ZSM-11, ZSM-12, ZSM-22, ZSM-23, ZSM-35, and ZSM-48, with mordenite framework inverted (MFI) type zeolites, such as ZSM-5 and ZSM-11, being particularly preferred. Generally, the medium-pore size aluminosilicate zeolite constitutes at least 10 wt %, such as from about 25 wt % to about 100 wt % of the zeolitic component of the catalyst.

Large pore zeolites are generally defined as those having a pore size in excess of 7 Angstroms (e.g. greater than 7 Angstroms) and a Constraint Index less than 3. Suitable large pore zeolites for use in the present process include zeolite beta, MCM-22, zeolite Y, Ultrastable Y, REY and Ultrastable REY. Suitable amorphous cracking catalysts include alumina, zirconia, silica/alumina, and silica/zirconia. The large pore and amorphous cracking components are desirable since they facilitate cracking of molecules in the feed that are too large to enter the pore structure of a medium pore size zeolite.

Where the pyrolysis catalyst contains a large pore or amorphous cracking component in addition to the medium pore size zeolite, the former may be present as part of the same formulated particles as those containing the medium pore zeolite or may be present as separate formulated particles.

In addition to the active components, the catalyst normally comprises a binder or matrix material that is resistant to the temperatures and other conditions employed in the reactor. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the rate of reaction. These catalytically active or inactive materials may include, for example, naturally occurring clays, e.g., bentonite and kaolin, to improve the crush strength of the catalyst composition under commercial operating conditions. Other suitable matrix or binder materials include inorganic oxides selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Typically the catalyst contains a binder or matrix material in an amount ranging from 20 wt % to 90 wt % of the total catalyst.

Generally, at least medium pore zeolite catalyst employed in the pyrolysis reactor is phosphorus stabilized, which is conveniently achieved by impregnating the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 wt % and about 30 wt %. Suitable phosphorus compounds include, but are not limited to, phosphonic, phosphinous, phosphorus and phosphoric acids, salts and esters of such acids, and phosphorous halides. After contacting with one or more phosphorus-containing compounds, the catalyst is dried and the calcined in an inert atmosphere or in the presence of oxygen, for example, in air, at a temperature of about 150° C. to 750° C., preferably about 300° C. to 500° C., for at least 1 hour, preferably 3 to 5 hours.

Under the conditions specified above, the pyrolysis catalyst is effective to crack heavy molecules in the residual fraction, including polynuclear aromatics, to smaller molecules, such as mononuclear aromatics, as well as to dealkylate $C_8+$ single-ring aromatic hydrocarbons having at least one alkyl group containing two or more carbon atoms present in the second hydrocarbon stream or produced by the resid cracking. Such reactions include cracking of ethyltoluene, ethylxylene, and cumene to toluene, xylene, and benzene, respectively. The cracking is of course accompanied by production of ethylene and propylene. In addition, the catalyst is effective to transalkylate $C_8+$ single-ring aromatic hydrocarbons having at least two methyl groups in the feed. Thus, an exemplary reaction is transalkylation of xylene with benzene to produce toluene. Other reactions include cracking and aromatization of aliphatic hydrocarbons in the feed to produce lower olefins and additional aromatic compounds.

Apart from the desired reactions discussed above, the pyrolysis catalyst effects non-selective conversion of the feed to coke which deposits on the catalyst causing its deactivation. Thus, part of the catalyst is continuously or intermittently removed from the reactor and circulated to an oxidative regenerator, where coke is burnt from the catalyst. Additional fuel may be added to the regenerator to heat the catalyst to the required regeneration temperature and to provide a portion of the heat of reaction required for the pyrolysis reactions.

Treatment of the Catalytic Pyrolysis Product

The effluent from the catalytic pyrolysis reactor is a fourth hydrocarbon stream having an increased benzene and/or toluene content compared with said second stream and a $C_3-$ olefin by-product. The $C_3-$ olefins are recovered from the effluent for use as a chemical feedstock and the remainder of the effluent is then fed to a distillation system where the fourth hydrocarbon stream is conveniently separated into a lighter fraction rich in $C_4$ and $C_5$ hydrocarbons, a heavy fraction rich in $C_8+$ hydrocarbons, and an intermediate fraction which is composed mainly of $C_6$ and $C_7$ hydrocarbons.

The lighter and heavy fractions are typically recycled to the catalytic pyrolysis reactor, whereas the intermediate fraction is normally fed to an aliphatics extraction unit where the aliphatic portion of the intermediate fraction is removed by solvent extraction or selective adsorption. The $C_6$ and $C_7$ aliphatic hydrocarbons removed in the aliphatics extraction unit may be recycled to the catalytic pyrolysis reactor, whereas the remainder of the intermediate fraction, which is rich in benzene and toluene, is fed to a xylene production unit, optionally after hydrotreating to remove sulfur and/or nitrogen impurities. Some or all of the benzene contained in the intermediate fraction may be recovered as a product rather than being used to produce additional xylene.

Xylene Production

The toluene and, where present, benzene separated from the fourth hydrocarbon stream is fed to a methylation reactor where the aromatic feed is methylated, generally with methanol in the presence of a specific zeolite catalyst at a temperature between about 500° C. and about 700° C., preferably between about 500° C. and about 600° C., a pressure of between about 1 atmosphere and 1000 psig (100 kPa and 7000 kPa), a weight hourly space velocity of between about 0.5 and 1000, and a molar ratio of toluene to methanol (in the reactor charge) of at least about 0.2, e.g., from about 0.2 to about 20. The process is preferably conducted in the presence of added water such that the molar ratio of water to benzene/toluene+methanol in the feed is between about 0.01 and about 10.

The zeolite catalyst employed in the alkylation process is selected to have a Diffusion Parameter for 2,2-dimethylbutane of about 0.1 to 15 $sec^{-1}$, and preferably 0.5 to 10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient ($cm^2$/sec) and r is the crystal radius (cm). The required diffusion parameters can be derived from sorption measurements provided the assumption is made that the plane sheet model describes the diffusion process.

Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q, D is the diffusion coefficient ($cm^2$/sec) and r is the crystal radius (cm). Graphical solutions for the plane sheet model are given by J. Crank in "The Mathematics of Diffusion", Oxford University Press, Ely House, London, 1967.

The zeolite employed in the present alkylation process is normally a medium-pore size aluminosilicate zeolite. Medium pore zeolites are generally defined as those having a pore size of about 5 to 7 Angstroms, such that the zeolite freely sorbs molecules such as n-hexane, 3-methylpentane, benzene and p-xylene. Preferably the medium pore zeolites have a Constraint Index of about 3 to about 12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are preferred for the present alkylation process since the size and shape of their pores favor the production of p-xylene over the other xylene isomers. However, conventional forms of these zeolites have Diffusion Parameter values in excess of the 0.1 to 15 $sec^{-1}$ range referred to above. However, the required diffusivity for the catalyst can be achieved by severely steaming the catalyst so as to effect a controlled reduction in the micropore volume of the catalyst to not less than 50%, and preferably 50% to 90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, preferably selected from oxides of the elements of Groups IIA, IIIA, IIIB, IVA, IVB, VA, and VIA of the Periodic Table (IUPAC version). Most preferably, said at least one oxide modifier is selected from oxides of boron, magnesium, calcium, lanthanum, and most preferably phosphorus. In some cases, it may be desirable to combine the zeolite with more than one oxide modifier, for example, a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 wt % and about 20 wt %, and preferably is between about 0.1 wt % and about 10 wt %, based on the weight of the final catalyst.

Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 wt % and about 30 wt %. Suitable phosphorus compounds include, but are not limited to, phosphonic, phosphinous, phosphorus and phosphoric acids, salts and esters of such acids, and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3 to 5 hours. Similar techniques known in the art can be used to incorporate other modifying oxides into the catalyst employed in the alkylation process.

In addition to the zeolite and modifying oxide, the catalyst employed in the alkylation process may include one or more binder or matrix materials resistant to the temperatures and other conditions employed in the process. Such materials include active and inactive materials such as clays, silica, and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the porous crystalline material can be composited with a porous matrix material such as silica-alumina, silica-magnesia, silica-zirconia, silica-thoria, silica-beryllia, silica-titania, as well as ternary compositions, such as silica-alumina-thoria, silica-alumina-zirconia silica-alumina-magnesia, and silica-magnesia-zirconia.

The relative proportions of porous crystalline material and inorganic oxide matrix vary widely, with the content of the former ranging from about 1% to about 90% by weight and more usually, particularly when the composite is prepared in the form of beads, in the range of about 2 wt % to about 80 wt % of the composite. Preferably, the matrix material comprises silica or a kaolin clay.

The alkylation catalyst used in the present process may optionally be precoked. The precoking step is preferably carried out by initially utilizing the uncoked catalyst in the toluene methylation reaction, during which coke is deposited on the catalyst surface and thereafter controlled within a desired range, typically from about 1 wt % to about 20 wt % and preferably from about 1 wt % to about 5 wt %, by periodic regeneration by exposure to an oxygen-containing atmosphere at an elevated temperature.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range of from about 400° C. to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The methylation process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

Using the present process, toluene can be alkylated with methanol so as to produce para-xylene at a selectivity of at least about 80 wt % (based on total $C_8$ aromatic product) at a per-pass toluene conversion of at least about 15 wt % and a trimethylbenzene production level less than 1 wt %. The olefin-rich light gas by-product may be recovered in a dedicated olefins recovery unit or routed to a steam cracker olefins recovery section. Unreacted toluene, methanol and a portion of the water product may be recycled to the methylation reactor and heavy byproducts routed to fuels disposition or recycled to the pyrolysis reactor. The $C_8$ fraction is routed to a para-xylene recovery unit, which typically operates by fractional crystallization or by selective adsorption (e.g., Parex or Eluxyl) to recover a para-xylene product stream from the alkylation effluent and leave a para-xylene-depleted stream containing mainly $C_7$ and $C_8$ hydrocarbons. The para-xylene-depleted stream is conveniently recycled to the pyrolysis reactor, generally after removal of any toluene for recycle to methylation step.

The invention will now be more particularly described with reference to the accompanying drawing and the following non-limiting Examples.

Figure 1:
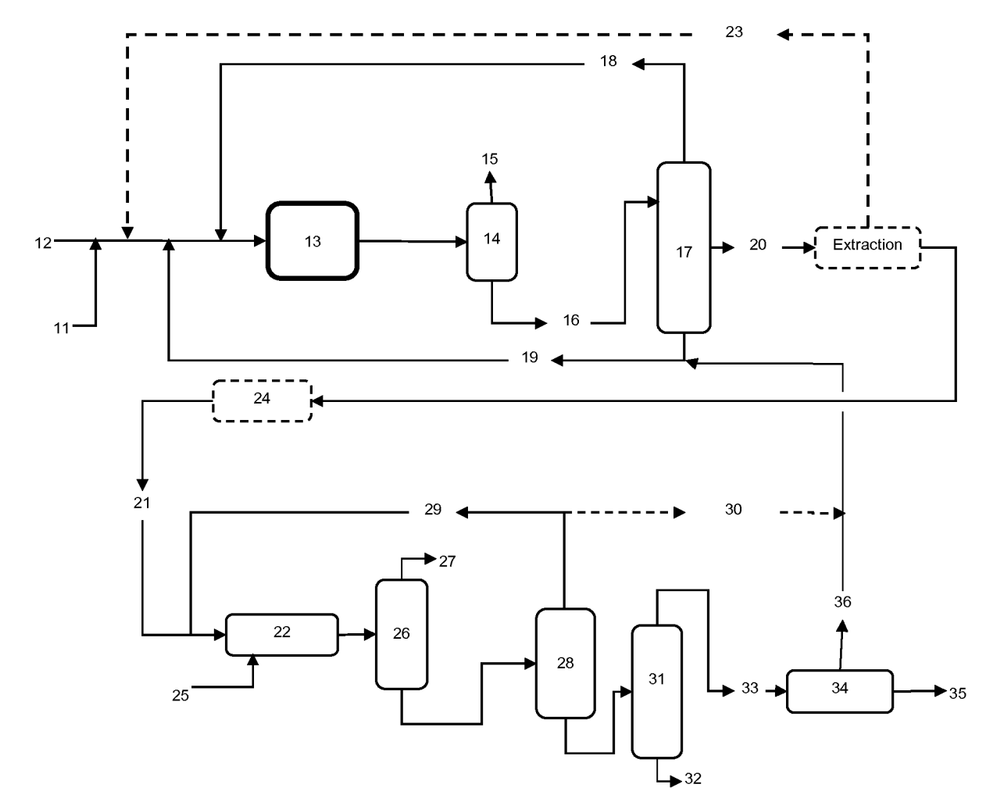
FIG. 1 is a schematic drawing of a hydrocarbon upgrading process according to a first embodiment of the present invention.

Referring to FIG. 1, in a first embodiment of the present process, a raw $C_4$ to $C_{12}+$ aliphatic and aromatic hydrocarbon product from a steam cracker (not shown) is fed by line 11 for blending with a residual fraction in line 12. The resultant blend is fed to a catalytic pyrolysis reactor 13 where the blend is cracked, transalkylated and aromatized in the presence of the pyrolysis catalyst to produce a gaseous hydrocarbon effluent. The gaseous effluent from the reactor 13 is fed to a separator 14 where the $C_4+$ components are condensed and ethylene and propylene are removed as gaseous product stream 15.

The liquid condensate from the condenser 14 is fed by line 16 to a first distillation unit 17 where the condensate is separated into a lighter fraction rich in $C_4$ and $C_5$ hydrocarbons, a heavy fraction rich in $C_8+$ hydrocarbons and an intermediate fraction which is composed mainly of $C_6$ and $C_7$ hydrocarbons. The lighter and heavy fractions are recycled via lines 18 and 19 respectively to the reactor 13, whereas the intermediate fraction is fed by lines 20, 21 to a methylation reactor 22, optionally after extraction and recycle of aliphatic components to the reactor 13 through line 23 and optionally after removal of sulfur in a hydrotreater 24.

Methanol is supplied via line 25 to methylation reactor 22 where it reacts with benzene and toluene in the intermediate fraction in line 21 to selectively produce para-xylene together with an olefin-rich light gas. The effluent from the methylation reactor 22 is then fed to a separator 26, from which the light gas is recovered as product stream 27. The remainder of the methylation effluent is fed to a second distillation unit 28, where unreacted $C_6$ and $C_7$ hydrocarbons are removed via overhead line 29 and recycled to the reactor 22. Optionally, part of the unreacted $C_6$ and $C_7$ hydrocarbons can be purged by recycle to the catalytic pyrolysis reactor 13 via line 30. The bottoms from the second distillation unit 28 are then fed to a third distillation unit 31 where the $C_9+$ fraction from the methylation effluent is removed via bottoms line 32 for recycle to the catalytic pyrolysis reactor 13.

The overhead from the third distillation unit 31 is rich in $C_8$ fraction from the methylation effluent and is fed by line 33 to a para-xylene recovery unit 34, where a para-xylene product stream is recovered in line 35, to leave a para-xylene-depleted stream which is recycled to the catalytic pyrolysis reactor 13 via line 36.

This invention further relates to:

1. A hydrocarbon upgrading process comprising:
    (a) treating a hydrocarbon feed in at least one of a steam cracker, catalytic cracker, coker, hydrocracker, and reformer under suitable conditions to produce a first stream comprising olefinic and aromatic hydrocarbons;
    (b) recovering from said first stream a second stream composed mainly of $C_4$ to $C_{12}$ olefinic and aromatic hydrocarbons;

(c) blending said second stream with a residual fraction from a steam cracker or an atmospheric or vacuum distillation unit to produce a third stream;

(d) catalytically pyrolyzing said third stream in a reactor under conditions effective to produce a fourth stream having an increased benzene and/or toluene content compared with said second stream and a $C_3$-olefin by-product;

(e) recovering $C_3$-olefins from said fourth stream; and (f) recovering benzene and/or toluene from said fourth stream.

2. The process of paragraph 1, further comprising preheating the second stream before or after the blending (c).

3. The process of paragraph 1 or 2, further comprising hydrotreating the residual fraction before or after the blending (c).

4. The process of paragraph 1, 2, or 3, wherein the catalytic pyrolysis is conducted in the presence of a catalyst comprising ZSM-5 and under reaction conditions including a temperature of about 480° C. to about 750° C.

5. The process of paragraph 4, wherein the catalyst further comprises a large pore and/or an amorphous cracking component.

6. The process of any of paragraphs 1 to 5, wherein the catalytic pyrolysis is conducted in a riser reactor.

7. The process of any of paragraphs 1 to 6, wherein part of the catalyst is removed from the reactor and contacted with an oxygen-containing stream to remove coke from the catalyst and heat the catalyst thereby providing a portion of the heat required for (d).

8. The process of any of paragraphs 1 to 7, further comprising removing $C_4$ and $C_5$ hydrocarbons from the fourth stream and recycling said $C_4$ and $C_5$ hydrocarbons to (d).

9. The process of any of paragraphs 1 to 8, further comprising removing $C_8+$ hydrocarbons from the fourth stream and recycling said $C_8+$ hydrocarbons to (d).

10. The process of any of paragraphs 1 to 9, wherein benzene and/or toluene are recovered from said fourth stream by separating a $C_6$ and/or $C_7$ fraction from the fourth stream and removing aliphatic hydrocarbons from the $C_6$ and/or $C_7$ fraction to leave an aliphatic depleted fraction.

11. The process of paragraph 10, wherein said aliphatic hydrocarbons are removed from the $C_6$ and/or $C_7$ fraction by solvent extraction or selective adsorption.

12. The process of paragraph 10 or 11, wherein said aliphatic hydrocarbons are recycled to (d).

13. The process of paragraph 10, 11 or 12 wherein said aliphatic depleted fraction is hydrotreated before recovery of said benzene and/or toluene.

14. The process of any of paragraphs 1 to 13, further comprising:

(g) methylating benzene and/or toluene recovered in (f) with a methylating agent to produce a xylene-enriched stream.

15. The process of paragraph 14, wherein said methylating is para-selective.

16. The process of paragraph 14 or 15, wherein said methylating agent is methanol.

17. The process of any of paragraphs 14 to 16, further including:

(h) recovering para-xylene from said xylene-enriched stream.

18. The process of any of paragraphs 1 to 17, wherein the residual fraction comprises heavy tar produced as the product of steam cracking and/or the bottoms product of a vapor liquid separator drum integrated into the steam cracker.

Example 1

This Example provides the estimated results of employing the process shown in FIG. 1 to upgrade 2529 kta of a $C_4$ to $C_{10}$ steam cracked product having the composition given in Table 1 which had been blended with 2529 kta of atmospheric resid of Daqing crude. The $C_3-$ olefin by-product recovered via line 15 and 27 was composed of 1296 kta of ethylene, 1590 kta propylene, and 456 kta of saturates. The C6/7 fraction in line 21 contained 666 kta of benzene and 1380 kta of toluene. The amount of para-xylene product recovered via line 35 was 2003 kta.

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of may be substituted therefor.

What is claimed is:

1. A hydrocarbon upgrading process comprising:

(a) treating a hydrocarbon feed in at least one of a steam cracker, catalytic cracker, coker, hydrocracker, and reformer under suitable conditions to produce a first stream comprising olefinic and aromatic hydrocarbons;

(b) recovering from said first stream a second stream composed mainly of $C_4$ to $C_{12}$ olefinic and aromatic hydrocarbons;

(c) blending said second stream with a residual fraction from a steam cracker or an atmospheric or vacuum distillation unit to produce a third stream;

(d) catalytically pyrolyzing said third stream in a reactor under conditions effective to produce a fourth stream having an increased benzene and/or toluene content compared with said second stream and a $C_3$-olefin by-product;

(e) recovering $C_3$-olefins from said fourth stream; and (f) recovering benzene and/or toluene from said fourth stream.

2. The process of claim 1, further comprising preheating the second stream before or after the blending (c).

3. The process of claim 1, further comprising hydrotreating the residual fraction before or after the blending (c).

4. The process of claim 1, wherein the catalytic pyrolysis is conducted in the presence of a catalyst comprising ZSM-5 and under reaction conditions including a temperature of about 480° C. to about 750° C.

5. The process of claim 4, wherein the catalyst further comprises a large pore and/or an amorphous cracking component.

6. The process of claim 1, wherein the catalytic pyrolysis is conducted in a riser reactor.

7. The process of claim 1, wherein part of the catalyst is removed from the reactor and contacted with an oxygen-containing stream to remove coke from the catalyst and heat the catalyst thereby providing a portion of the heat required for (d).

8. The process of claim 1, further comprising removing $C_4$ and $C_5$ hydrocarbons from the fourth stream and recycling said $C_4$ and $C_5$ hydrocarbons to (d).

9. The process of claim 1, further comprising removing $C_8+$ hydrocarbons from the fourth stream and recycling said $C_8+$ hydrocarbons to (d).

10. The process of claim 1, wherein benzene and/or toluene are recovered from said fourth stream by separating a $C_6$ and/or $C_7$ fraction from the fourth stream and removing aliphatic hydrocarbons from the $C_6$ and/or $C_7$ fraction to leave an aliphatic depleted fraction.

11. The process of claim 10, wherein said aliphatic hydrocarbons are removed from the $C_6$ and/or $C_7$ fraction by solvent extraction or selective adsorption.

12. The process of claim 11, wherein said aliphatic hydrocarbons are recycled to (d).

13. The process of claim 10, wherein said aliphatic depleted fraction is hydrotreated before recovery of said benzene and/or toluene.

14. The process of claim 1, further comprising:
(g) methylating benzene and/or toluene recovered in (f) with a methylating agent to produce a xylene-enriched stream.

15. The process of claim 14, wherein said methylating is para-selective.

16. The process of claim 14, wherein said methylating agent is methanol.

17. The process of claim 14, further including:
(h) recovering para-xylene from said xylene-enriched stream.

18. The process of claim 1, wherein the residual fraction comprises heavy tar produced as the product of steam cracking and/or the bottoms product of a vapor liquid separator drum integrated into the steam cracker.

* * * * *